US008107703B2

(12) United States Patent
Shekhar et al.

(10) Patent No.: US 8,107,703 B2
(45) Date of Patent: Jan. 31, 2012

(54) QUANTITATIVE REAL-TIME 4D STRESS TEST ANALYSIS

(75) Inventors: Raj Shekhar, Elkridge, MD (US); Vivek Walimbe, Pewaukee, WI (US)

(73) Assignees: University of Maryland, Baltimore, Baltimore, MD (US); Cleveland Clinic Foundation, Cleveland, OH (US)

( * ) Notice: Subject to any disclaimer, the term of this patent is extended or adjusted under 35 U.S.C. 154(b) by 563 days.

(21) Appl. No.: 12/371,111

(22) Filed: Feb. 13, 2009

(65) Prior Publication Data

US 2009/0161938 A1 Jun. 25, 2009

Related U.S. Application Data

(63) Continuation of application No. PCT/US2007/017972, filed on Aug. 14, 2007.

(60) Provisional application No. 60/837,515, filed on Aug. 14, 2006.

(51) Int. Cl.
*G06K 9/00* (2006.01)

(52) U.S. Cl. ............................ 382/128; 128/922; 378/4

(58) Field of Classification Search .................. 382/100, 382/128, 129, 130, 131, 132; 128/922; 378/4–27
See application file for complete search history.

(56) References Cited

U.S. PATENT DOCUMENTS 7,043,062 B2 * 5/2006 Gerard et al. ................ 382/128
7,043,063 B1 * 5/2006 Noble et al. .................. 382/128
7,526,112 B2 * 4/2009 Murphy et al. ............... 382/128
7,536,042 B2 * 5/2009 Murphy et al. ............... 382/128
7,653,227 B2 * 1/2010 Krishnan et al. ............. 382/128
7,693,563 B2 * 4/2010 Suresh et al. ................ 600/407
7,945,080 B2 * 5/2011 Rinck et al. .................. 382/131
2005/0010117 A1 1/2005 Agutter et al.
2005/0143654 A1 6/2005 Zuiderveld et al.
2005/0240094 A1 10/2005 Pichon et al.
2006/0100502 A1 5/2006 Chen et al.
2007/0167784 A1 7/2007 Shekhar

OTHER PUBLICATIONS

"FPGA Accelerated Deformable Image Registration for Improved Target-Delineation during CT-Guided Interventions", Omkar Dandekar and Raj Shekhar, IEEE Transactions on biomedical Circuits and Systems, 1(2): 2007, 11 pgs.

(Continued)

*Primary Examiner* — Anand Bhatnagar
(74) *Attorney, Agent, or Firm* — Evans & Molinelli, PLLC; Eugene Molinelli

(57) ABSTRACT

Stress test analysis is facilitated through the acquired and manipulated use of a sequence of volumetric data regarding the heart (and may particularly comprise the left ventricle) for the assessment of the health state of the heart. Several provided and illustrated examples specifically relate to ultrasound volumetric data, but the volumetric data may be obtained through the use of any imaging modality (e.g., CT, MRI, X-ray, PET, SPECT, etc.) or combination thereof, and may be used to compute one or more functional quantitative metrics (e.g., ejection fraction.) The volumetric data may also be used to render one or more views of the heart, and particularly of the left ventricle. This disclosure relates to these and other uses of such volumetric data, and to some various implementations thereof, such as methods, systems, and graphical user interfaces.

20 Claims, 11 Drawing Sheets

OTHER PUBLICATIONS

"PET guidance for liver radio frequency ablation: An evaluation", Peng Lei, Omkar Dandekar, Faaiza Mahmoud, David Widlus, Patrick Malloy and Raj Shekhar, Proc. of SPIE, vol. 6509, 2007, 8 pgs.

"PET/CT-guided interventional procedures: rationale, justification, initial study, and research plan", Kenneth Wong, Sara Petrillo, Filip Banovac, Joseph Rahill, Elliot Levy, Raj Shekhar, David Earl-Graef and Kevin Cleary, International Journal of computer Assisted radiology and Surgery, vol. 2, Supplement 1, Jun. 2007, 2 pgs.

International Search Report, International Application No. PCT/US207/017972, International Filing Date Aug. 14, 2007, 2pgs.

* cited by examiner

200

QUANTITATIVE REAL-TIME 4D STRESS TEST ANALYSIS

RELATED APPLICATION(S)

This application is a continuation of PCT/US07/17972 filed Aug. 14, 2007, which claims benefit of provisional application Ser. No. 60/837,515, filed Aug. 14, 2006, the entirety of which is incorporated herein by reference.

STATEMENT REGARDING FEDERALLY FUNDED RESEARCH

The U.S. Government has a paid-up license in this invention and the right in limited circumstances to require the patent owner to license others on reasonable terms as provided for by the terms of Grant No. DAMD17-99-1-9034 awarded by the U.S. Department of Defense. This statement is included in accordance with the requirements of 35 U.S.C. 202(c)(6).

BACKGROUND

Coronary artery disease (CAD) remains a leading cause of death in the United States. Early and accurate detection of myocardial ischemia with underlying CAD has the potential to reduce morbidity and mortality in patients by identifying left ventricular (LV) regions that could be treated before the corresponding myocardium becomes irreversibly scarred.

SUMMARY

The following presents a summary of some of the disclosure herein. This summary is not an extensive overview, and is intended to neither identify key and/or critical aspects, features and/or elements nor delineate the scope of the claimed subject matter. Its purpose is merely to act as a prelude to the more detailed description that is presented later.

Left ventricle (LV) assessment facilitated through acquired and manipulated use of volumetric data spanning at least one complete cardiac cycle regarding the left ventricle, such as may be gathered during a cardiac stress test. The volumetric data may be used to compute a functional quantitative metric pertaining to the heart. The volumetric data may also be used to produce one or more views of the heart that may facilitate evaluation by healthcare providers. The present disclosure relates to techniques for such uses of volumetric data, and to implementation thereof, such as (e.g.) methods, systems, and graphical user interfaces (GUIs) that operate in accordance with the principles discussed herein. Several exemplary sequences of volumetric data mentioned herein refer to data collected through the use of ultrasound imaging modality, but these techniques are is also applicable to similar analysis of sequence of volumetric data obtained through the use of any other imaging modality (e.g., CT, MRI, X-ray, PET, SPECT, etc.)

To the accomplishment of the foregoing and related ends, the following description and annexed drawings set forth certain illustrative aspects of the claimed subject matter. These aspects are indicative, however, of but a few of the various ways in which one or more of the principles of the claimed subject matter may be employed. Other advantages and/or novel features of the claimed subject matter may become apparent from the following detailed description, and when considered in conjunction with the drawings.

DETAILED DESCRIPTION

Figure 1A:
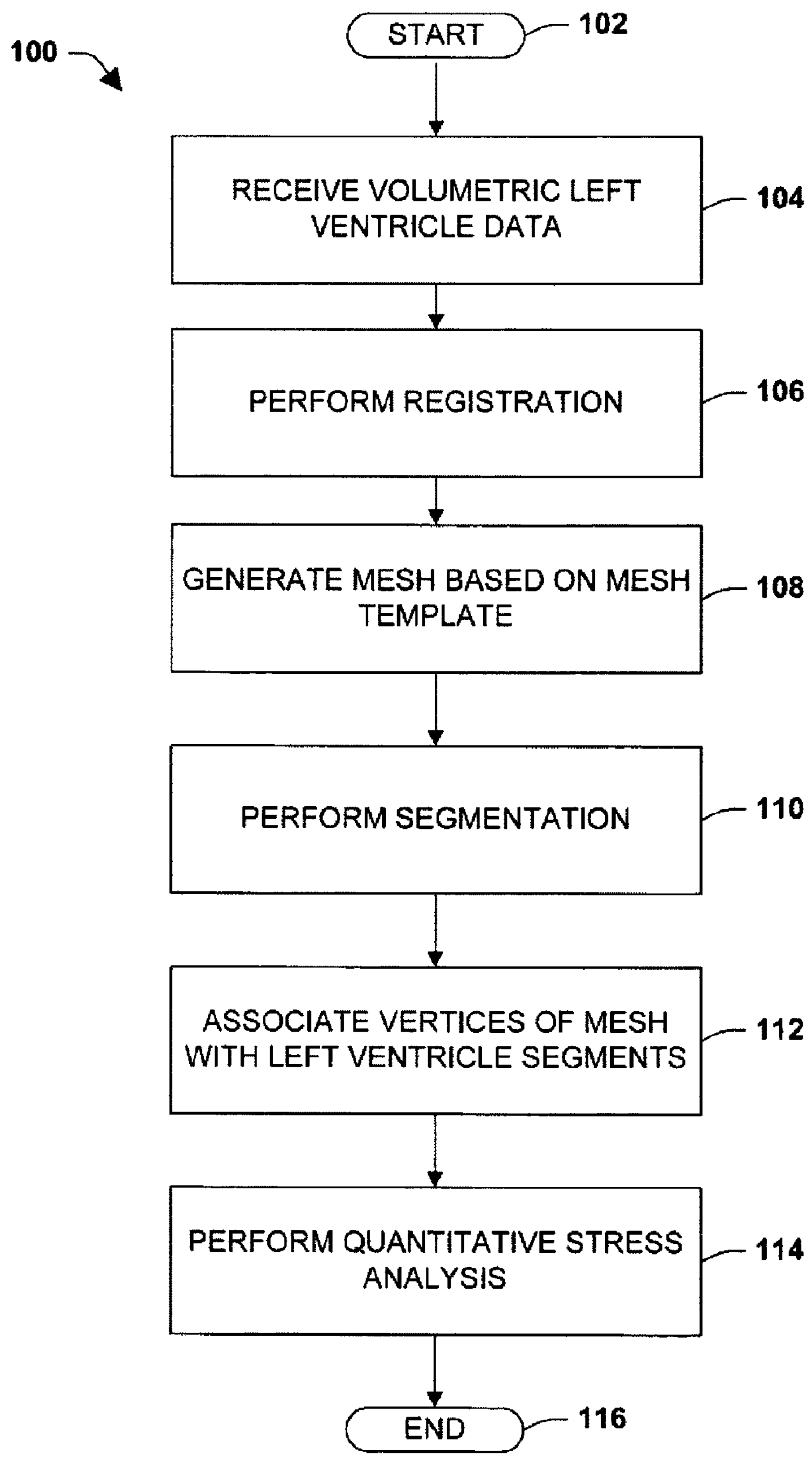
FIG. 1A is a flow diagram illustrating an exemplary method for heart assessment utilizing volumetric data.

In the following, reference is made to the drawings, wherein like reference numerals are generally utilized to refer to like elements throughout, and wherein the various structures are not necessarily drawn to scale. For purposes of explanation, numerous specific details are set forth in order to provide a more thorough understanding. It may be evident, however, to one skilled in the art that one or more aspects may be practiced with a lesser degree of these specific details. In other instances, well-known structures and devices are shown in block diagram form to facilitate understanding.

Coronary artery disease (CAD) causes more than two thirds of heart failures and is the leading cause of morbidity and mortality in the United States. The mortality is significantly greater if CAD, as opposed to nonischemic diseases such as valvular heart disease, is the underlying cause of left ventricle (LV) dysfunction. Fortunately, CAD and LV dysfunction do not always signal irreversible myocardial damage, and normal heart function may be restored after medical (drug) therapy or revascularization. The selection of the most effective treatment option, critical to reducing current mortality and morbidity rates, rests on the timely and accurate diagnosis of CAD as the cause of LV dysfunction.

Even a modest 1% gain in sensitivity and specificity of diagnosis of CAD would have a tremendous economic impact. With 1% specificity improvement, 1% of CAD patients would escape unnecessary catheterizations—an estimated annual savings of approximately $539 million ($24,893 [average per catheterization]×21,660 [1% of annual CAD discharges]). With a 1% sensitivity gain, the same number of CAD patients currently misdiagnosed would receive appropriate treatment, saving $1.22 billion ($56,803/patient) in mortality and morbidity costs. Although the exact cost savings can be debated, there is no question that these would be significant given the numbers of men and women suffering from CAD. The disclosure herein relates to LV assessment as part of stress testing, which can promote early and/or accurate detection of myocardial ischemia with underlying CAD. This may, in turn, facilitate more accurate treatment decisions resulting in reduced morbidity and mortality.

Stress testing is a technique employed to diagnose myocardial ischemia, a state of imbalance between blood supply and demand caused by narrowing of the coronary arteries. Stressing the heart raises the myocardial oxygen demand, and the failure to meet this demand (in the presence of CAD) elicits symptoms such as metabolic and perfusion abnormalities and abnormal LV wall motion and thickening. These symptoms are absent in the healthy heart, which, upon stress, is hyperperfused, becomes hyperdynamic, and contracts more forcefully. These stress-induced symptoms are two early clinical symptoms of CAD. In individuals with known or suspected CAD, abnormal LV motion and thickening are indications of myocardial ischemia.

Turning to FIG. 1A, a flowchart depicting an example method 100 for facilitating stress analysis of a heart is provided that operates in accordance with the principles discussed herein. The method 100 begins at 102 and involves receiving 104 volumetric data representing the left ventricle. The method 100 also involves registering 106 the volumetric data to obtain at least one of temporally and spatially aligned volumetric data representing the left ventricle. The method 100 also involves applying 108 a mesh template to the registered volumetric data to produce at least one mesh comprising a plurality of vertices. The method 100 also involves segmenting 110 the registered volumetric data to produce a plurality of left ventricle segments. The method 100 also involves associating 112 the vertices of the mesh with the left ventricle segments. The method 100 also involves computing 114 a functional quantitative metric based on the at least one mesh and left ventricle segments. Having achieved these steps, the method 100 provides a functional quantitative metric that facilitates stress analysis of the heart, and therefore the method 100 ends at 116.

Figure 1B:
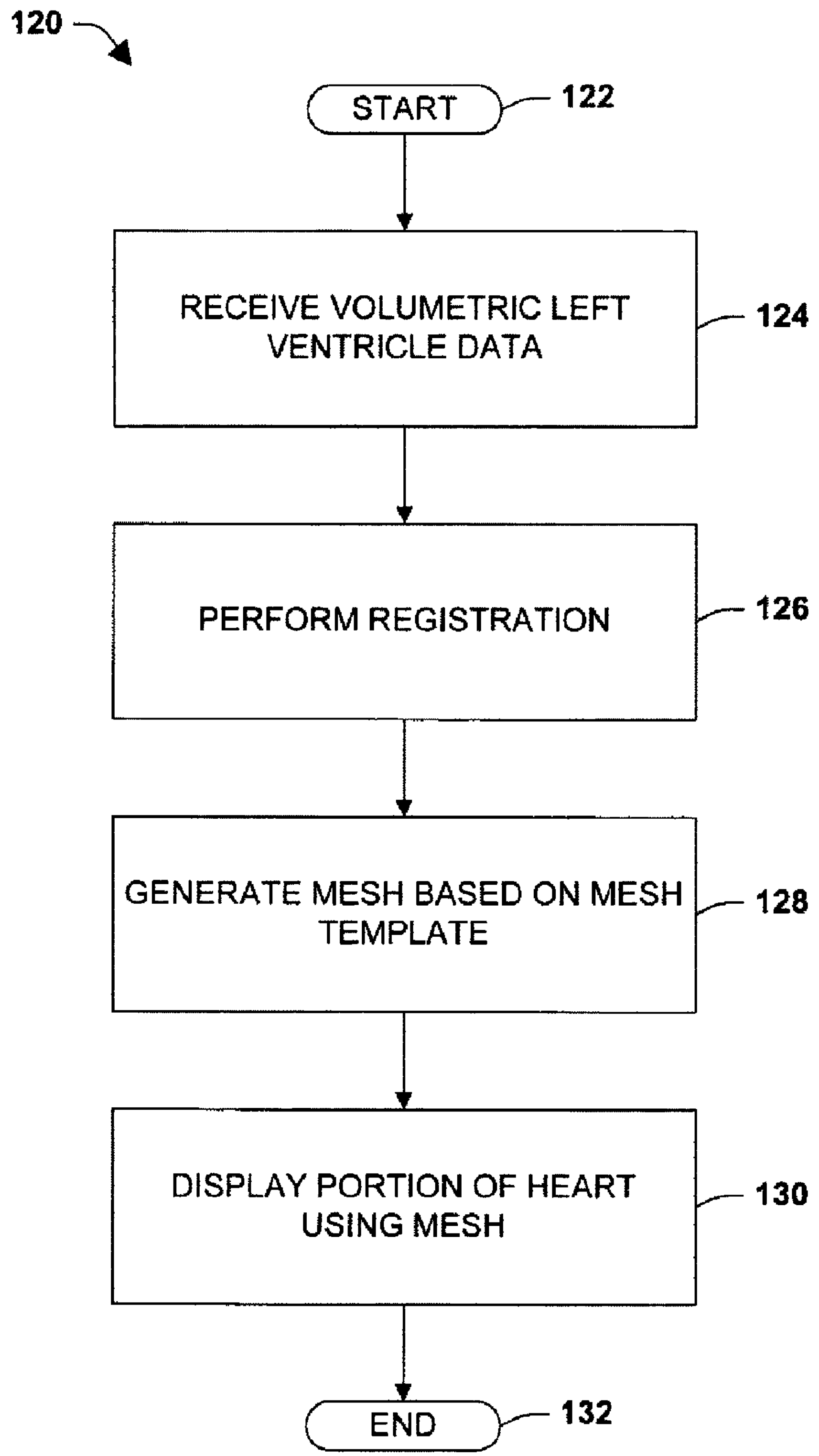
FIG. 1B is a flow diagram illustrating another exemplary method for left ventricle (LV) assessment utilizing volumetric data.

FIG. 1B presents a flowchart illustrating an exemplary method 120 for displaying a view of a portion of a heart in accordance with the techniques discussed herein. This exemplary method 120 begins at 122 and involves receiving 124 volumetric data of the left ventricle. The method 120 also involves registering 126 the volumetric data to obtain at least one of temporally and spatially aligned volumetric data representing the left ventricle. The method 120 also involves applying 128 a mesh template to the registered volumetric data to produce at least one mesh comprising a plurality of vertices. The method 120 also involves displaying 130 the view of the portion of the heart on the at least one mesh. Having generated the view of the portion of the heart, the method 120 ends at 132.

As will be discussed, some or all of the methods illustrated in FIGS. 1A and/or 1B may make use of various modalities, such as three-dimensional (3D) ultrasound or 3D echocardiography (generally referred to herein as 3D data). Although 3D echocardiogram data is primarily referred to herein, it is to be appreciated that this disclosure is not meant to be limited to such data. Rather, any type of 3D data, such as MRI, CT, X-ray, PET, SPECT, etc., for example, can be processed as described herein. While the methods illustrated in these figures are as a series of acts or events, it will be appreciated that the illustrated ordering of such acts or events are not to be interpreted in a limiting sense. For example, some acts may occur in different orders and/or concurrently with other acts or events with or apart from those illustrated and/or described herein. Also, not all illustrated acts may be required to implement one or more aspects. Further, one or more acts may be carried out in one or more separate acts and/or phases. In addition, some or all of the method may be computer implemented and/or implemented as hardware or a combination of hardware and software.

After initialization (e.g., where flags and/or pointers may be set), three-dimensional (3D) ultrasound or 3D echocardiography image data is received/obtained regarding the LV. This 3D LV data includes both pre- and post-stress image data. The heart, and thus the LV, can be stressed, for example, by having the patient exercise and/or by administering certain drugs to the patient. It will be appreciated that 3D ultrasound/echocardiography is capable of very fast imaging, and can thus scan the entire left ventricle along with its complex motion in a few cardiac cycles. This provides substantially comprehensive visualization of the left ventricle, rather than just a few planar sections as is the case with conventional image data acquisition mechanisms.

In one example, a 3D echocardiography scanner can acquire full LV volumetric data in the form of 4 conical subvolumes scanned during 4-7 consecutive heartbeats from the same transducer position, which are then integrated into complete pyramidal image sets using electrocardiographic (ECG) gating. The short acquisition time at peak stress using 3D ultrasound makes post-stress imaging convenient and fast and facilitates consistent stress level as well as the potential to capture fleeting and short-lived wall motion abnormalities.

In another example, 3D echocardiography volumetric images can be collected at a rate of between about 20 and about 30 frames/second, where this collection rate may vary as a function of scan depth. The scan depth can be kept between about 12 and about 16 cm, depending on the size of the patient's heart. The field of view (FOV) can be kept fixed before and after stress and set so that the entire left ventricle remains visible in the frames. The number of frames will typically range between about 10 and about 25 depending on the heart rate.

It can be appreciate that misalignment can occur between pre- and post-stress images due to, among other things, movement of the patient and/or the fact that a sonographer cannot precisely duplicate ultrasound probe location and orientation between image acquisitions. Net misregistration has an undesirable component and a desirable component. The undesirable component corresponds to the coordinate system mismatch between pre- and post-stress 3D ultrasound acquisitions resulting from probe placement differences and patient repositioning. The desirable component includes the stress-induced changes, which are useful for assessing the stress-induced changes to the LV.

Registration is performed to mitigate misalignment. It will be appreciated that misalignment correction (registration) improves the quality of information used for diagnostics, at least, by relieving a sonographer from the "stress" of attempting to make a geometric match between scans, so that he or she can concentrate on obtaining higher quality images and capturing important wall motion abnormalities. Misalignment mitigation is accomplished, at least, by temporal and spatial registration of pre- and post-stress image sets.

Figure 2:
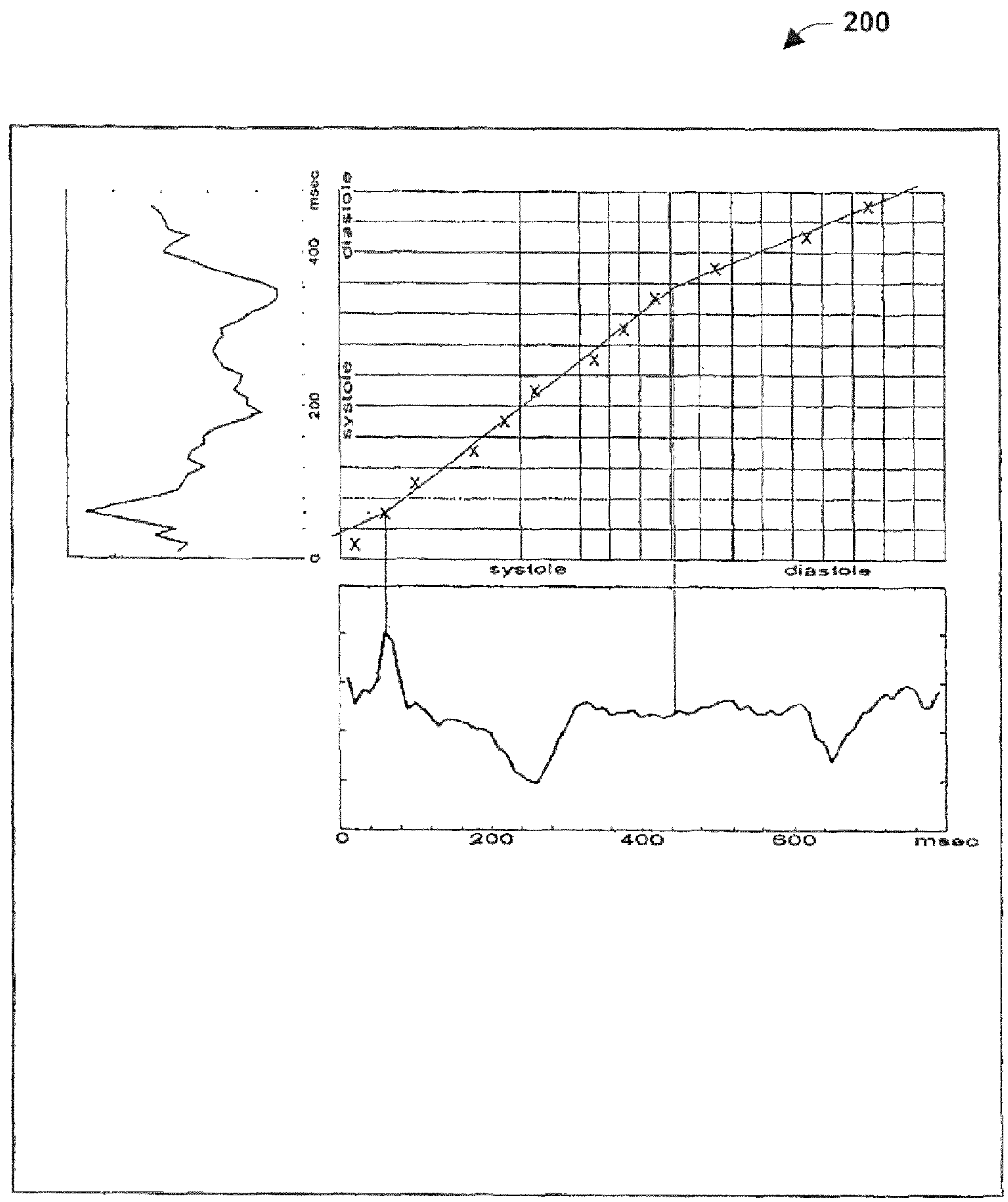
FIG. 2 is a graph illustrating temporal alignment of pre- and post-stress 3D image data regarding the LV.

Registration begins with temporal alignment, which helps create pre- and post-stress image pairs belonging to the same cardiac phase, helping to account for the different numbers of frames between pre- and post-stress data sets, as well as uneven shrinkage of the durations of diastole and systole when heart rate increases, as is the case during stress. Temporal alignment implements an interpolation function that takes on a piecewise linear shape. This is illustrated in FIG. 2 where temporal alignment using pre- and post-stress echocardiograms are plotted along the horizontal (x) and vertical (y) axes, respectively, of graph 200. A piecewise linear interpolation function facilitates phase by phase matching when the heart rate differs. All in all, respective pre-stress frames closest in cardiac phase to post-stress frames are found through temporal alignment.

Registration continues with spatial alignment, where respective phase-correlated/temporally aligned image pairs are spatially aligned using a two sequence process that facilitates retaining the stress induced anatomical changes. This registration uses mutual information measurements of image similarity. Respective pairs yield a solution upon spatial registration, and a unique transformation is found by computing the median of image similarities for the respective solutions. Transforming respective frames of the post-stress sequence by the median solution aligns the pre- and post-stress data sets and is analogous to having acquired the post-stress sequence from a slightly different probe location (given by a translation part) and orientation (given by a rotation part). It is important to note that image registration does not alter original image shape/intensities. Rather, it merely reorients the post-stress image sequence as if it were collected from the same probe location and orientation as during pre-stress acquisition.

Figure 3:
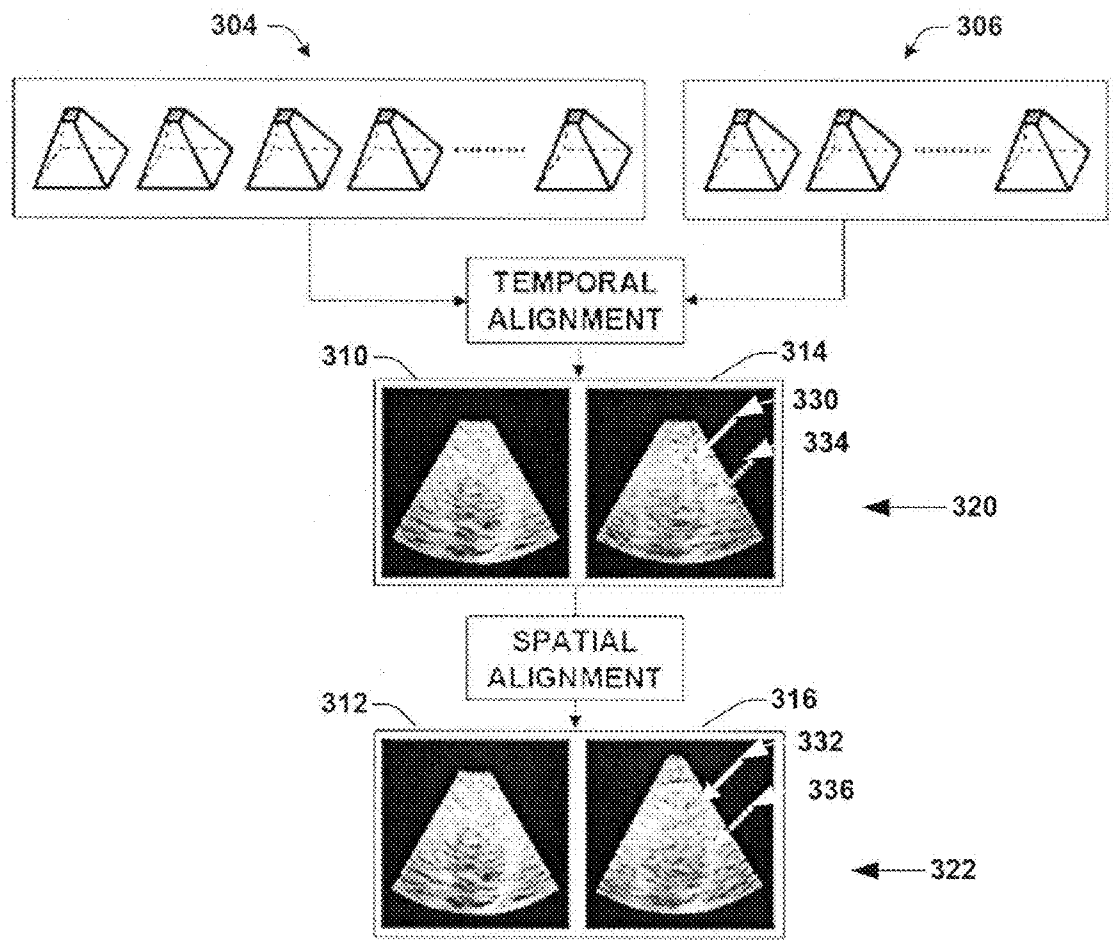
FIG. 3 is a diagram illustrating temporal and spatial alignment of pre- and post-stress 3D images regarding the LV.

FIG. 3 illustrates 3D data received and registered. For example, a plurality of conical volumes 302 indicative of 3D data for consecutive heartbeats are illustrated pre-stress 304 and post-stress 306. Images on the left 310, 312 correspond to pre-stress images, while images on the right 314, 316 correspond to post-stress images. Temporal alignment produces multiple phase-correlated pre-310 and post 314 stress image pairs 320, while spatial alignment mitigates coordinate system mismatch between images while maintaining stress-induced changes. The solid 330, 332 and dotted 334, 336 arrows in images 314 and 316 illustrate the effect of registration. That is, solid arrows 330, 332 point to the same location in the 2D image in 314 and 316, and dotted arrows 334, 336 similarly point to the same image locations in 314 and 316. Note improved matching of the LV wall (as pointed by the solid and dashed arrows) in 316 compared with 314 following image registration. It can be appreciated that image registration thus improves the quality of information used for assessment, which, in turn, may raise the accuracy of diagnosis.

After registration segmentation can be performed. Segmentation is performed utilizing a dual voxel plus wiremesh template, which comprises a 3D image (voxel template) and a corresponding manually delineated LV endocardial surface (wiremesh template), where the endocardial surface corresponds to the inner wall of the LV. The voxel template is initially registered with the end-diastolic frame of the image sequence to be segmented using a mutual information-based approach, and the resulting transformation is used to initialize the wiremesh template substantially close to the final solution in the image being segmented. The initialized wiremesh template is then refined iteratively to snap substantially to the actual endocardium under the joint influence of mesh-derived internal forces and image-derived external (gradient vector flow-based) forces. That is, model-based segmentation starts with placing a wiremesh template of the expected shape in the vicinity of the (perceived) borders of the LV. Energy minimization then refines the wiremesh template appropriately under image-derived and shape integrity-preserving constraints to make it snap substantially to the true borders. Model-based segmentation is suitable for ultrasound images because it is robust with respect to intensity dropouts and noise. In one example, model-based segmentation can be enhanced with automatic initial placement of the shape template and segmentation of 3D shapes. A dual "voxel+wiremesh" template is implemented which is an end-diastolic volumetric image with the endocardial surface carefully traced by an expert. Initial placement of the shape template is facilitated by registering the voxel template with the ultrasound volume to be segmented. Applying the resultant transformation to the wiremesh template initializes it in proximity to the final solution. In one example, registration utilizes 8 parameters (3 translations, 3 rotations, and 2 scaling parameters along long and short axes) as a trade-off between registration complexity and robustness. This can be further refined using energy minimization, which is guided by internal forces that maintain the overall LV shape and external forces that drive the wiremesh template toward 3D edges corresponding to LV endocardium. It will be appreciated that respective endocardial meshes are obtained for the cardiac sequence by repeating this process. This allows the shape of the LV to be tracked throughout the cardiac cycle.

The endocardial mesh for respective frames is then divided into multiple segments for individual scoring and regional analysis. In one example, the mesh is divided into 16 (old convention of the ASE) or 17 (new convention of the ASE) segments. The subdivision information is encoded in the wiremesh template. Using a priori information, respective vertices of the wiremesh template are manually tagged for the LV wall subdivisions to which they belong. During segmentation of the cardiac sequence, wiremesh for respective frames is initialized by propagation of the result of segmentation of the preceding frame. The vertices of the wiremesh retain their tag and accompanying information during the propagation of results over successive frames. The initialized wiremesh for respective frames is then independently refined in 3D spatial coordinates. Upon completion of refinement, vertices with the same tag are joined to recreate the LV subdivisions. By retaining segment tag information during propagation of results over successive frames, spatio-temporal continuity is retained for individual segments over the cardiac cycle. Further, since the individually tagged vertices of the wiremesh have freedom to move in the 3D spatial domain during refinement under spatial constraints imposed by forces ensuring mesh integrity, the changes in shape, size, and orientation of individual segments due to scaling and gradual torsional motion of the LV are inherently incorporated into a sequence of wiremeshes representing the final segmentation over the cardiac cycle.

Figure 4:
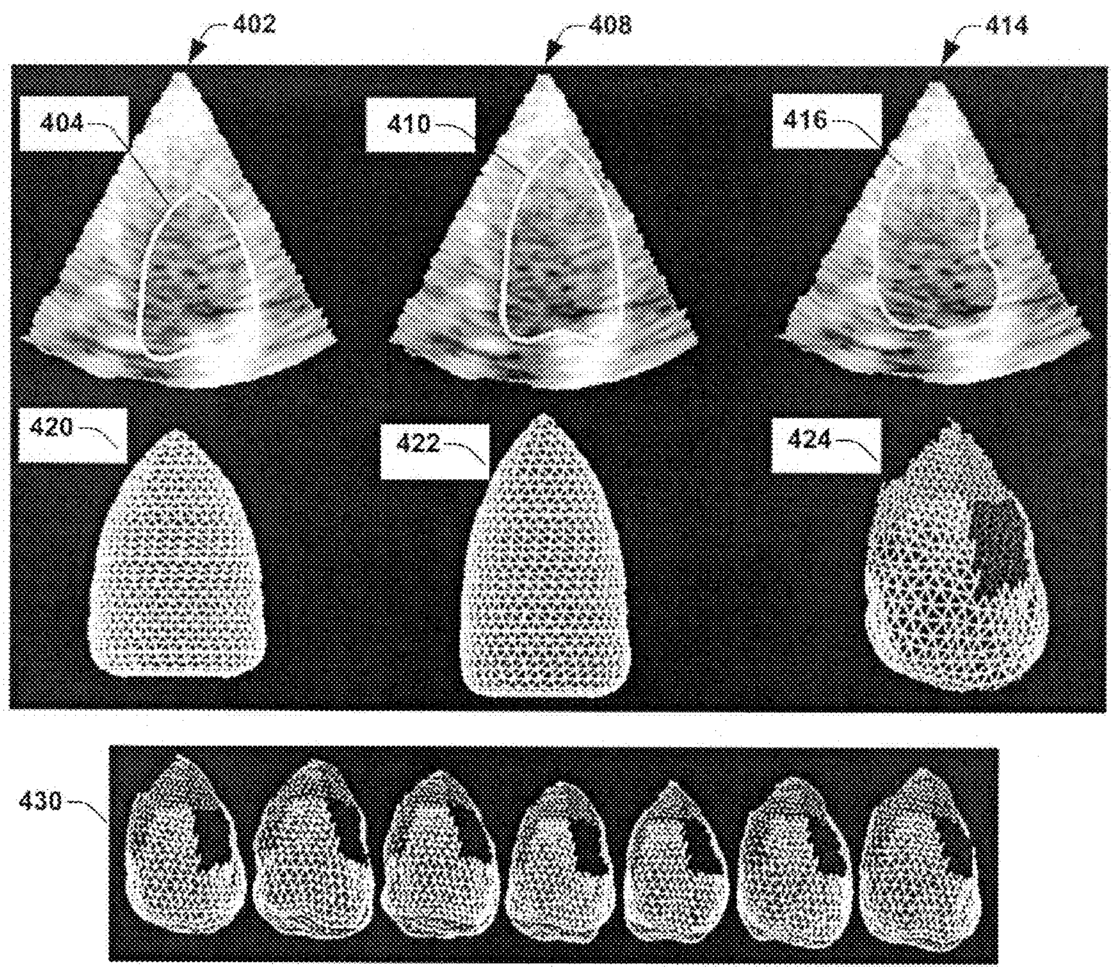
FIG. 4 illustrates images depicting segmentation and modification of 3D wiremesh templates therein.

FIG. 4 illustrates segmentation and the modification of 3D wiremesh templates therein. In image 402, for example, contour 404 illustrates the position of the endocardial mesh template before initialization. In image 408, contour 410 illustrates the position of the endocardial mesh template after registration-assisted initialization with LV image template. In image 414, contour 416 illustrates the final result of endocardial segmentation obtained by internal and external force-based refinement of the initialized template. Images 420, 422, and 424 illustrate 3-dimensional renderings of endocardial mesh corresponding to images 402, 408 and 414, respectively. The bottom group of images 430 illustrates segmented volumetric shapes corresponding to different phases of a cardiac cycle (obtained by registration-assisted segmentation of respective frames as illustrated in images 402, 408, 414, 420, 422, and 424). It will be appreciated that different colors can be associated with different segments of the LV to facilitate identifying these segments.

Figure 5:
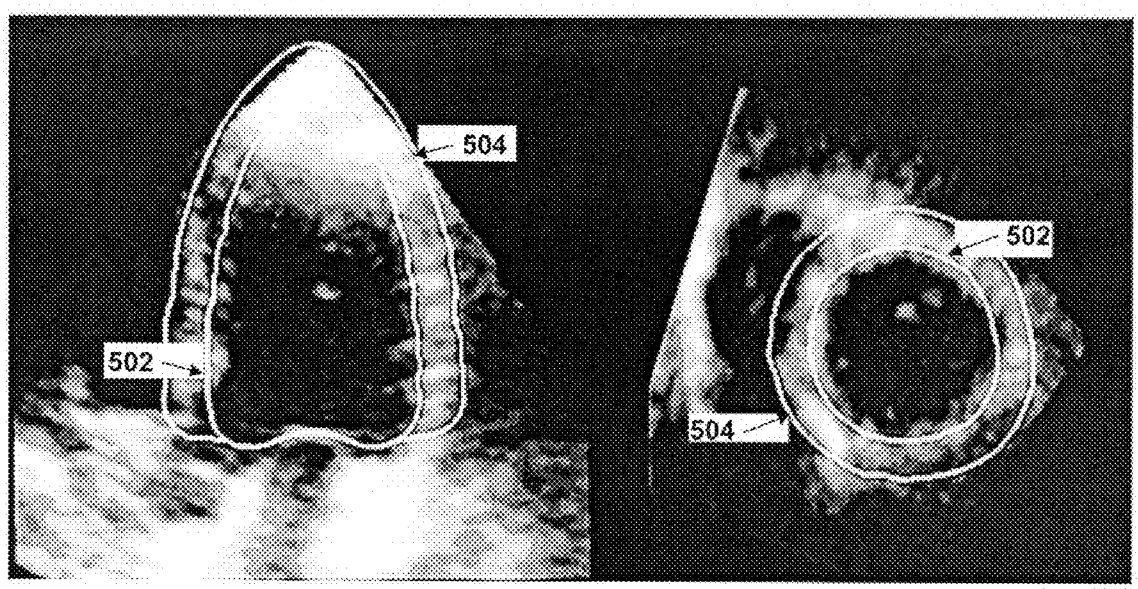
FIG. 5 illustrates images depicting segmentation of the epicardium and endocardium of the LV in a 2D slice view.

Epicardium segmentation can also then be performed by placing a shape template (showing expected LV cavity shape) within a 3D ultrasound image to be segmented and then refining it, where the epicardium corresponds to the outer layer of tissue of the LV. The epicardium can be rendered as a translucent surface, for example, so that the endocardium can be visualized concurrently. FIG. 5 illustrates one example where a shape template has two 3D wiremeshes, one for the endocardium 502 and another for the epicardium 504. The shape template can be created, for example, by tracing the endo- and epicardial surfaces in a user-defined 3D ultrasound frame (template image). The manual tracing has to be done once as part of creating the segmentation infrastructure. Once a shape template (wiremesh) and the corresponding template image (voxel data) exist, no other manual acts are necessary. The epicardial mesh is configured to lay outside the endocardial mesh. Voxel-based registration performs initial placement of the dual mesh in a new image. Both meshes are refined concurrently. Constraints can be implemented to maintain the expected separations, including those during disease conditions, between the inner and outer meshes. To segment multiple frames to follow the motion of the LV wall, results from respective frames can be propagated to the next frame and mesh refinement repeated. Division into multiple (e.g., 17 (or 16)) nonoverlapping segments can then be performed, and individual vertices of the endo- and epicardium wiremesh templates tagged as belonging to one of the divided segments. After segmentation of the underlying 3D image sequence, multiple (e.g., 17) segments are generated by grouping those vertices that have the same tag.

Once segmentation is performed LV assessment can be performed with an implemented graphical user interface. By way of example, this may include using the endocardial meshes to determine quantitative metrics, such as LV volume curves, ejection fraction, 3D segmental excursions, and/or segmentwise fractional area change, for example, and presenting one or more of these to a user. That is, once the multiple LV segments are identified in pre- and post-stress frames, parameters for quantitative diagnosis can be computed. For example, the 3D excursion of respective segments can be computed by measuring the net displacement of the center of the segment over a single cardiac cycle, and the fractional area change for respective segments can be computed by following the segments throughout a cardiac cycle. The per-segment wall thickness can be computed as the average distance between endo- and epicardial surfaces for a segment. Repeating this measurement for multiple frames can provide wall thickness variation(s) over the cardiac cycle. These parameters can be computed for both rest and stress sequences.

By way of further example, global LV functional quantitative measures, such as volume curves and ejection fraction, can be evaluated directly from the meshes representing the segmented LV myocardium. Once the individual LV segments are identified in all rest and stress frames, regional quantification of LV parameters is also possible. For example, the 3D segmental excursion can be computed by measuring the net displacement of the center of the segment over the cardiac cycle. The per-segment wall thickness can be computed by averaging distance between its endo- and epicardial surfaces. Percent wall thickening can be calculated as $$\frac{100\cdot(thickness_{systole}-thickness_{diastole})}{thickness_{systole}}.$$

Area of respective segments can be calculated by summing the area of respective triangular faces of the wiremesh belonging to particular segments. Segmental fractional area change can be calculated as $$\frac{100\cdot(area_{diastole}-area_{systole})}{area_{diastole}}.$$

Center of the left ventricle can be identified in respective frames as the center of the LV endocardial mesh, and respective parameters can be calculated with reference to this point. Thus, successful myocardial segmentation facilitates accurate quantitative analysis of global and local structure and function of the LV by calculation of parameters like wall thickness/thickening, fractional area change (for LV structure), LV volume, ejection fraction, and/or 3D wall-motion (for LV function)

Figure 6:
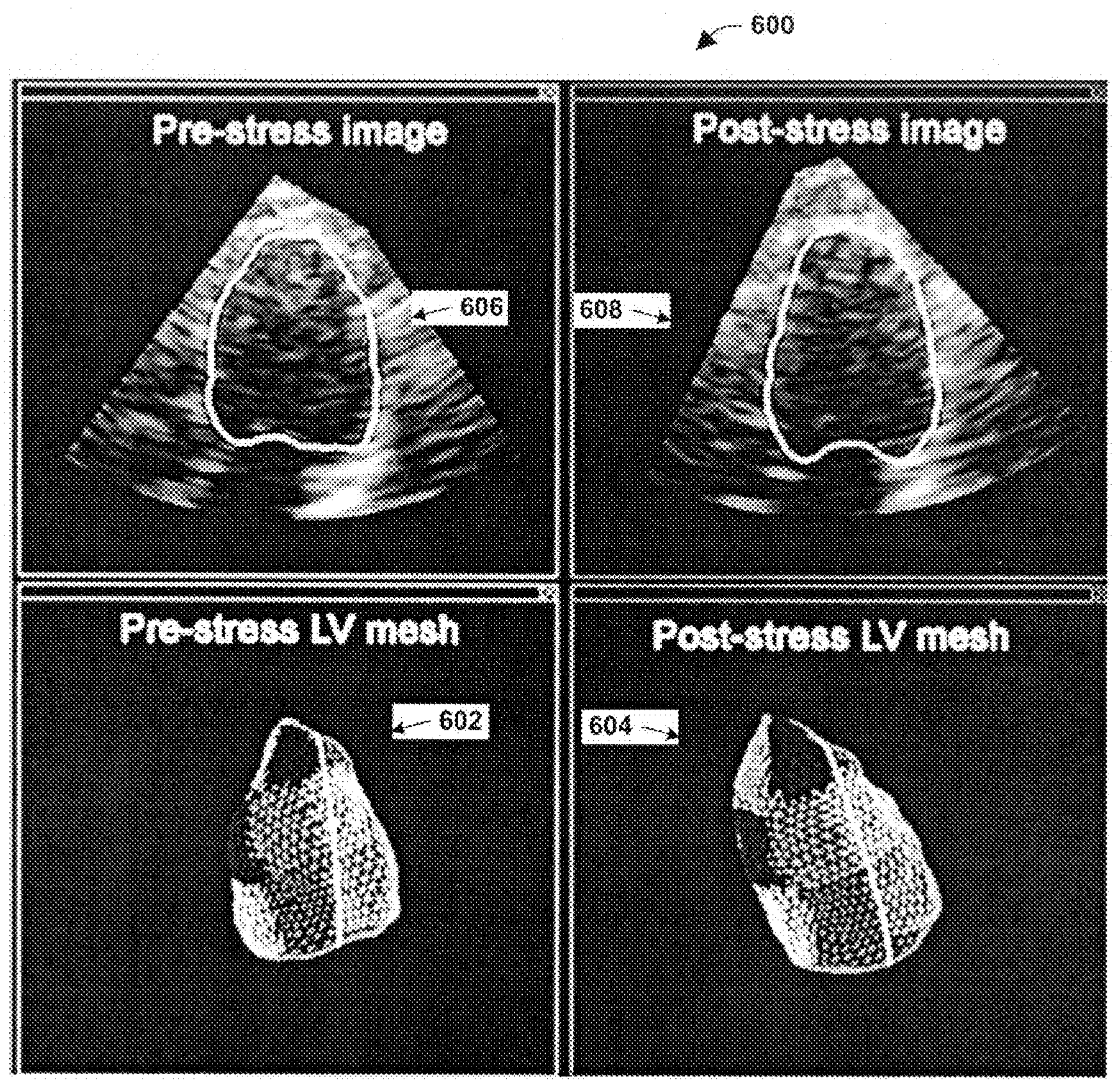
FIG. 6 illustrates a graphical user interface wherein pre- and post-stress LV images are presented in accordance with the disclosure herein.

FIG. 6 illustrates one type of graphical user interface that may be presented to a user. In the illustrated example, a side-by-side display 600 of pre- and post-stress images is presented to facilitate assessing the LV (e.g., to facilitate diagnosis of stress induced wall-motion abnormalities). It will be appreciated that a demarcation, such as a particular pattern and/or coloring, for example, may be overlaid on the endocardial mesh in lower images 602, 604 to track the position/orientation of the corresponding user-selected 2-dimensional cross-sectional views illustrated in upper images 606, 608, for example.

It will be appreciated that such interactive visualization facilitates improved LV assessment at least by providing more views of the heart as opposed to 3-4 cross-sectional views, for example. This also allows a user to visualize a "beating" cardiac cross-section or a slice through the RT3D ultrasound data sequence at the original frame rate (e.g., 15-25 frames/sec) and to vary this cross-section interactively to interrogate different regions of the left ventricle without stopping the cine-loop. This dynamic manipulation capability can be supported on a conventional desktop or laptop computer, for example, making it cost effective and more clinically feasible as compared to techniques that require special-purpose computers.

In a further example, real-time, interactive visualization of 3D echocardiography can be implemented whereby a default imaging plane through the periodic 3D data can be displayed, and a user can move to another plane by moving the computer mouse. Throughout this interaction, the images can be replayed at the original frame rate so as to maintain the original heart rate. It can display pre- and post-stress 3D stress echo data sets side-by-side. The two views can also be coupled so that varying the imaging plane in one view brings up the corresponding view in the other plane. In addition, the heart rates can be synchronized (e.g., peak-stress heart rate can be slowed to match the resting heart rate or resting heart rate can be accelerated to match the peak-stress heart rate or a combination of the two).

A user can thus view anatomically correlated pre- and post-stress views and interrogate regions of the left ventricle interactively. Dynamic (3D wiremesh) renderings of the LV both before and after stress are available during interactive visualization. The results of segmentation are also displayed in the form of an overlaid contour on respective cross-sectional images. A user can selectively focus on individual segments concurrently on the cross-sectional image and the wiremeshes, thus allowing the user to gain an understanding of the normality or abnormality of regional wall motion.

Figure 7:
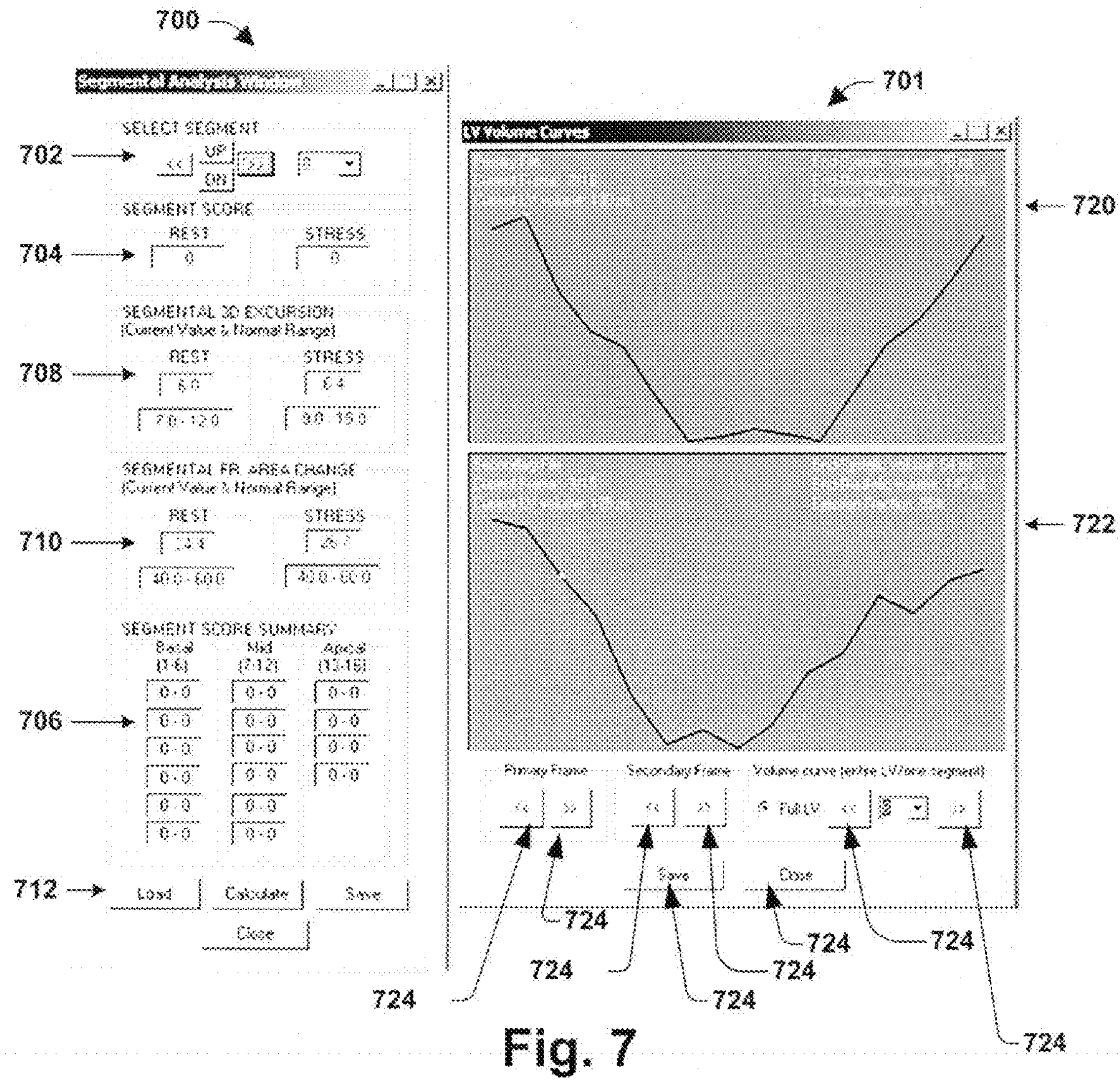
FIG. 7 illustrates a couple of graphical user interfaces wherein information related to one or more LV segments is presented in accordance with the disclosure herein.

FIG. 7 illustrates some other types of graphical user interfaces 700, 701 that can be presented to a user in accordance with the disclosure herein. These may, for example, be components of a wall motion analysis software suite. In the illustrated example, one of the graphical user interfaces 700 has an interface component 702 that allows a user to select a particular segment of the LV. This exemplary graphical user interface 702 includes a drop down menu, text entry box, and scroll buttons, but may include any other type of selection means. Another interface component 704 of this graphical user interface 700 allows at rest (pre-stress) and stress (post-stress) scores to be entered for particular segments. Such scores for different segments can be accumulated and displayed in a summary location 706 of the graphical user interface 700. By way of example, the scores may be assigned according to the standard ASE-recommended scheme: 1=normal, 2=hypokinetic, 3=akinetic, 4=dyskinetic, and 5=aneurysm. This allows a user to tabulate segmental wall motion scores.

The graphical user interfaces 700, 701 may also include locations where one or more metrics are displayed. In the illustrated example, values for 3D excursion 708 and fractional area change 710 are displayed. These values may, for example, be calculated and displayed automatically (e.g., by a microprocessor, processor, hosting computer, etc.) for a particular segment when a user highlights that segment (e.g., by clicking on it with a mouse and/or selecting it with a user interface component, such as 702, etc.). These values can be updated and displayed along with the normal ranges for respective measures as the user goes about selecting different segments. These values (and/or the backgrounds of the boxes within which they are displayed) may also be identified, e.g. by color-coding, to indicate whether the current values are within normal ranges, outside normal ranges, or on the border. This illustrated example of this part of the graphical user interface also includes buttons to load and save data and to calculate metrics (e.g., based upon newly loaded data).

In the illustrated example, another graphical user interface 701 (which may be part of a larger, more encompassing graphical user interface) displays volumetric curves for a particular segment of the LV. The upper curve 720 may correspond to an at rest situation, whereas the bottom curve 722 may correspond to a stress situation, for example. Interface components 724 (e.g., buttons) at the bottom of this graphical user interface facilitate navigation to selected frames and/or segments as well as the ability to save data and close this graphical user interface. It will be appreciated that graphical user interfaces such as the disclosure herein may be advantageous, as 3D image data can be acquired and manipulated, and then stored for subsequent examination/interaction, thus facilitating clinical processing. The tools comprising the graphical user interfaces allow a user to scan through multiple LV segments, where advancing to a new segment reorients the cross-sectional and 3D perspective views so that the segment in question is visualized, and its derived parameters and their reference values (normal range) displayed. This facilitates assessment of the LV.

Figure 8:
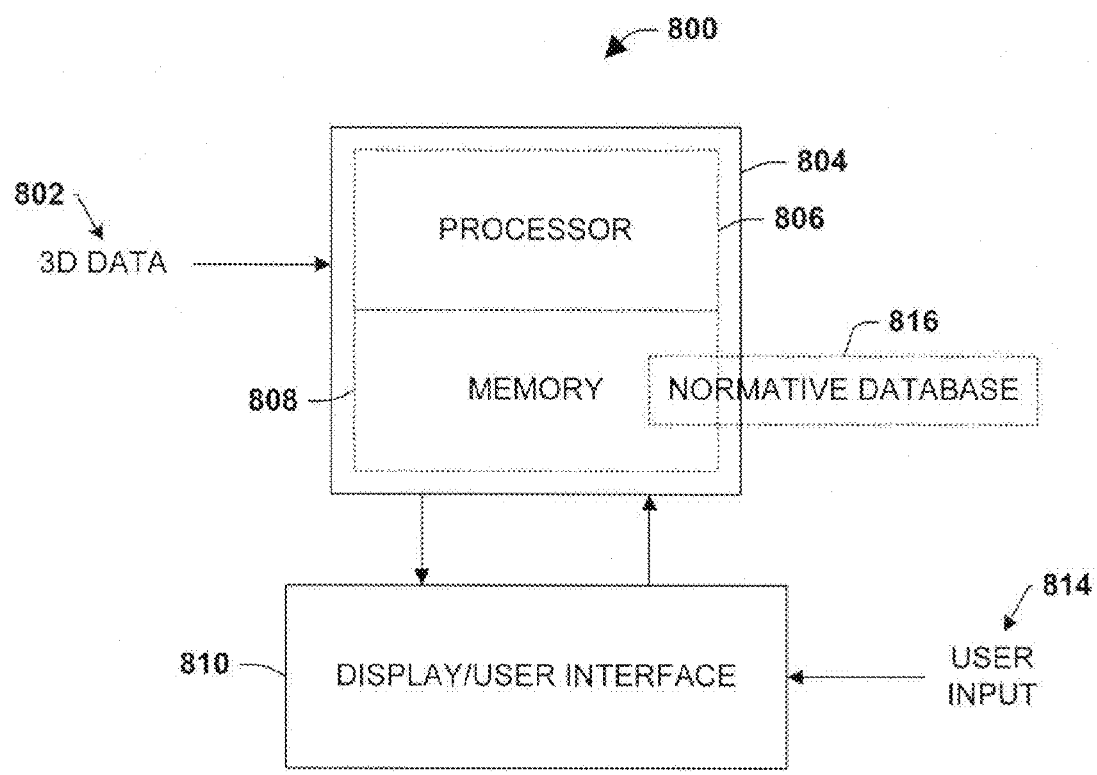
FIG. 8 illustrates a system wherein one or more aspects of a method for facilitating LV assessment can be implemented.

FIG. 8 illustrates an exemplary system 800 wherein at least some of the method 100 can be implemented. That is, acquired 3D image data of the LV 802 is fed into a computing component 804 comprising a processor 806 and memory 808 containing a data representation of a normative database 816. A display/user interface 810 is operatively coupled to the computing component 804 and is configured to display relevant information to a user, such as in the form of graphical user interfaces 600, 700, and/or 701, for example. User input 814, such as segment scores and/or particular segments selected, is provided to the system 800 via the display/user interface 810, which may include a mouse, touch screen, microphone with voice recognition software, etc., for example.

It will be appreciated that graphics processing units (GPU) resident on most modern video cards (included in such computing components 804) can be taken advantage in the processor 806, memory 808, and/or display/user interface 810 to accommodate the computational demands of dynamic interactive visualization involving large data size (e.g., 100-200 MB) as may be required by the method 100. That is, algorithms implemented herein may be configured to operate on GPU'S. A 3D texture-mapping module of GPUs is hardwired to interpolate among a 3D grid of data samples-a computation used to create rich-texture environments in video games. This 3D interpolation can also be utilized in plane visualization. Because texture memory may be too small to hold 3D stress test data, data bricking techniques and/or custom brick caching schemes can also be implemented to lower memory requirements and facilitate efficient utilization of memory. Data bricking and brick caching facilitate efficient memory utilization by storing those bricks (voxel sub-cubes) intersected by the current and upcoming cross-sections. In this manner, merely those voxels in the neighborhood of the displayed cross-section figure are utilized in interpolation mathematics, which may streamline the computation required to perform the method 100.

It can be appreciated that the usefulness of a measured diagnostic parameter may be enhanced if accompanied by a normal range of values (e.g., the normal ranges for 3D excursion 708 and fractional area change 710 metrics illustrated in FIG. 7). Accordingly, a normative database 816 is represented in the memory 808 to maintain such values. It will be appreciated that memory 808 may comprise any suitable form of volatile and/or non-volatile memory, such as (e.g.) system RAM, ROM, magnetic storage (e.g. a hard disk drive or RAID array), optical storage (e.g. optical disc), etc., or any combination thereof. The database 816 can be populated by compiling measured values in healthy individuals with disease-free hearts and artifact-free images, both at rest and during stress. As mentioned above, segment-wise measurements can then be compared to these norms to facilitate assessing the LV.

Figure 9:
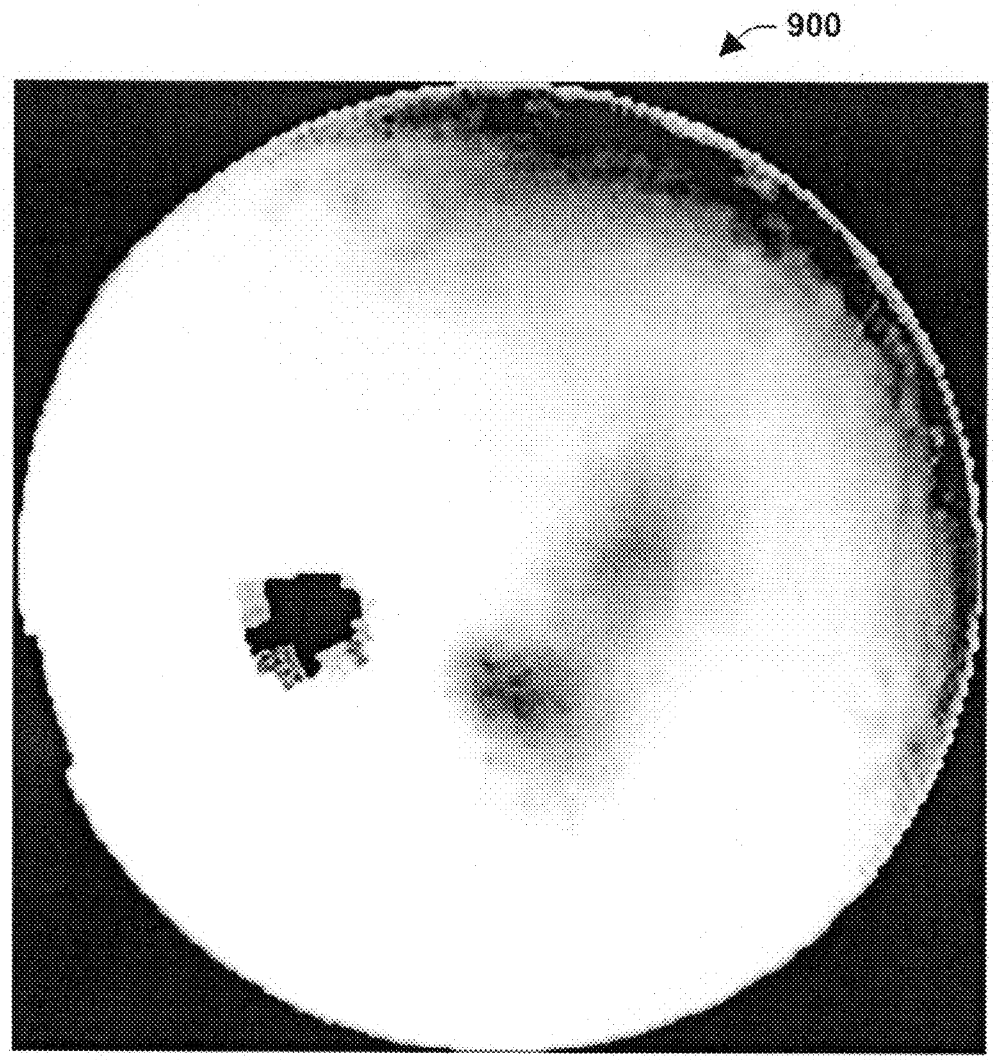
FIG. 9 illustrates an image wherein a derived metric of a LV segment is depicted in a bull's eye view.

FIG. 9 illustrates an exemplary bull's eye view 900 of derived parameters (e.g., 3D excursion, fractional area change, wall thickness, etc.) that can be generated to further facilitate assessing the LV. In the bull's-eye view 900, the 3D LV wall is mapped to a normalized circular shape so that different regions of the view correspond to different segments. Boundaries of the different segments can be superimposed, and color-coded information on derived parameters can be applied directly onto the beating LV wall.

It will be appreciated that some embodiments of the present disclosure may mitigate some many disadvantages associated with the prior art. By way of example, single-photon emission computed tomography (SPECT) that shows myocardial perfusion defects upon stress is prescribed as frequently as stress echo for the diagnosis of CAD. However, stress SPECT is a longer test that costs about 3 times more than stress echo. Magnetic resonance (MR) imaging, computed tomography (CT), and positron emission tomography (PET) are other potential alternatives to stress echo. However, these modalities are hampered by various aspects such as high costs, limited clinical use, and limited applicability (contraindications include pacemakers) for cardiac MR imaging, limited isotope availability and high costs coupled with limited reimbursement for PET, and risk of radiation exposure and low sensitivity for imaging myocardial ischemia for CT. Thus, stress echo as a scanning modality may provide an advantageous combination of economic viability and clinical suitability for the widest range of patients suspected of myocardial ischemia and underlying CAD.

Additionally some limitations of conventional stress echo that are rooted in its use of 2D ultrasound may be avoided by utilizing the 3D stress echo disclosed herein. For example the limited 60-90-second imaging window immediately after peak stress allows scanning no more than 4 cardiac cine-loops using 2D ultrasound. Because LV wall motion abnormalities are stress dependent and the stress level immediately begins to decline from the point of peak stress, the 4 cine-loops may not correspond to the same stress level, and may fail to capture a fleeting wall motion abnormality. With only 3-4 planar views of the heart available, clinicians may miss the diseased LV wall segments or fail to appreciate the full extent of the disease. Even with acceptable quality of imaging, comparison of wall motion at identical locations in pre- and post-stress images is necessary for a precise diagnosis. The pre-/post-stress image pairs, however, are often misaligned because of practical difficulties in duplicating the exact location and orientation of the ultrasound probe on the chest in a procedure that, by necessity, involves a great deal of patient motion. Additionally, interpretation of the resulting images remains subjective and based on visual estimates, resulting in only moderate intra- and interobserver and interinstitution agreement.

In accordance with the disclosure herein, after image acquisition, pre- and post-stress image sequences can be registered and segmented, and per-segment parameters can be calculated before a user reads them. Image analyses may be performed immediately after data acquisition. The results may be stored and made available for diagnosis, for efficient integration into clinical workflow. A computer based display capability and/or graphical user interface allows a user to interactively visualize cross-sections through pre- and post-stress data sets by merely moving a computer mouse, for example. This allows a user to cycle through and analyze individual LV wall segments and corresponding quantitative parameters. The user can assign individual segmental scores on a 1-5 scale, for example, and is aided by visualization of pre- and post-stress regional wall motion and unique measurements on segment-wise parameters, including their normal ranges.

Figure 10:
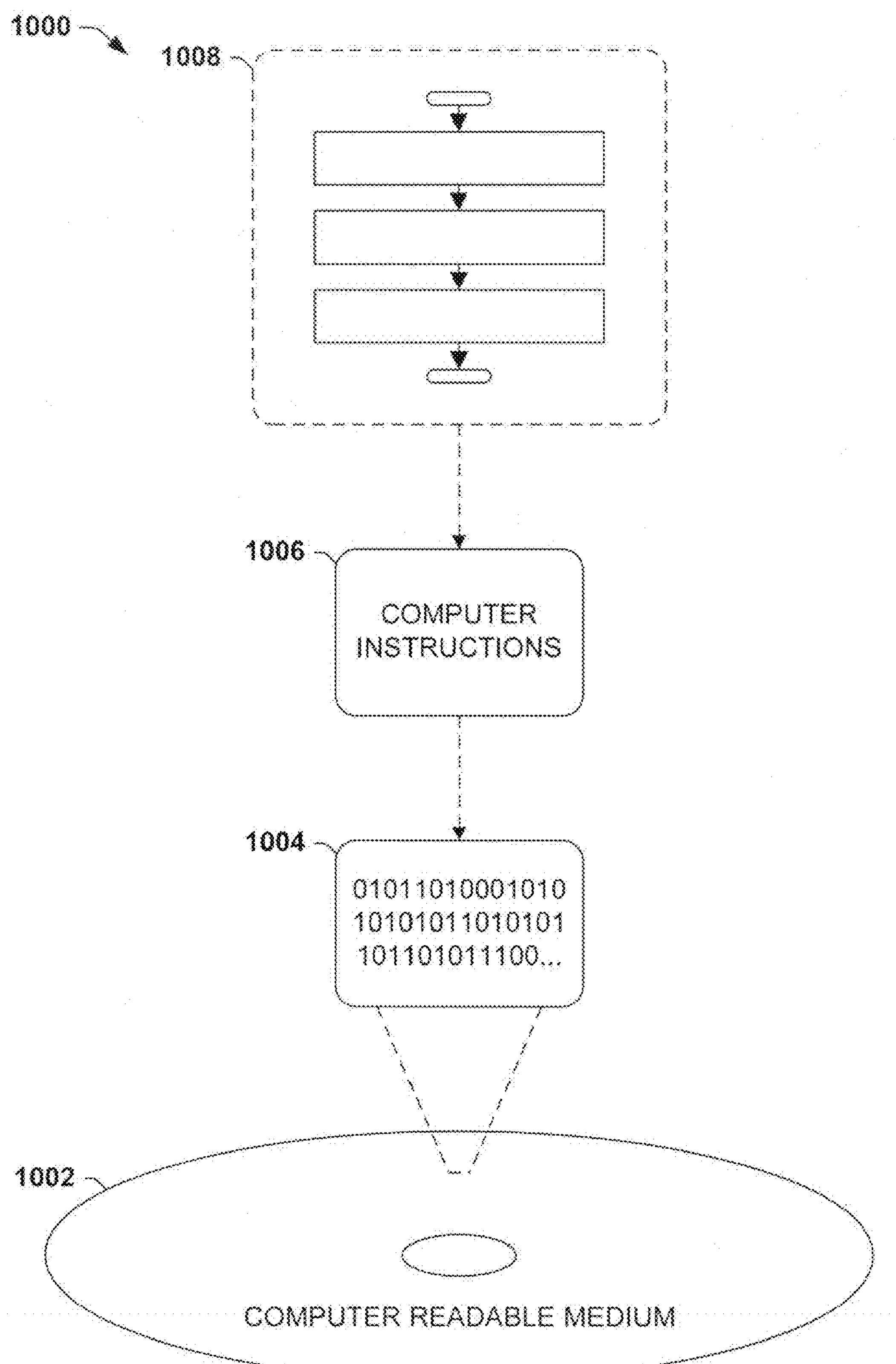
FIG. 10 illustrates an exemplary computer-readable medium comprising processor-executable instructions.

The techniques discussed herein may also be embodied as a computer-readable medium comprising processor-executable instructions configured to facilitate stress analysis of a heart as discussed herein. An exemplary computer-readable medium that may be devised in these ways is illustrated in FIG. 10, wherein the implementation 1000 comprises a computer-readable medium 1002 (e.g., a CD-R, DVD-R, or a platter of a hard disk drive), on which is encoded computer-readable data 1004. This computer-readable data 1004 in turn comprises a set of computer instructions 1006 configured to operate according to the principles 1008 set forth herein. In one such embodiment, the processor-executable instructions 1006 may be configured to perform a method of facilitating stress analysis of a heart, such as the method illustrated in the flowchart of FIG. 1A, and/or a method of displaying a view of a portion of a heart, such as the method illustrated in the flowchart of FIG. 1B. In yet another embodiment, the processor-executable instructions 1006 may be configured to implement one or more graphical user interfaces, such as the graphical user interfaces illustrated in FIG. 6 and/or FIG. 7. Many such computer-readable media may be devised by those of ordinary skill in the art that are configured to operate in accordance with the techniques presented herein.

It will be appreciated that the description herein is at times represented in terms of processes and symbolic representations of operations by conventional computer components (e.g., central processing unit (CPU), microprocessor and/or processor associated with a general purpose computer system, memory storage devices for the CPU, connected pixel-oriented display devices). These symbolic representations are a means used by those skilled in the art of computer programming and computer construction to convey teachings and discoveries to others skilled in the art. For the purposes of this discussion, a process or method is generally considered to be a sequence of computer-executed steps leading to a desired result. These steps usually require manipulations of physical measurable quantities (e.g., electrical, magnetic, optical signals capable of being stored, transferred, combined, compared). Those skilled in the art use various terms to refer to these quantities (e.g., as bits, values, elements, symbols, characters, text, terms, numbers, records, files). It should be understood that manipulations within the computer are often referred to with various terms (e.g., adding, comparing, moving) that are often associated with manual operations performed by a human operator. The operations described herein may be performed in conjunction with a human operator or user that interacts with the computer or computers.

It should be understood that the examples described herein are not limited to any particular computer, program, apparatus or language type (e.g., assembly, machine, compiled, interpreted). Additionally, the software and hardware configurations set forth herein are not limited to any specific hardware or software configuration. Rather, the systems and methodologies described herein can be implemented on a wide variety of hardware and software platforms (e.g., specialized apparatus to perform the systems and methods described herein, dedicated computer systems with hard-wired logic or programs stored in memory, graphics processor units (GPUs), discrete logic devices, large scale integrated circuits (LSIs), application-specific integrated circuits (ASICs), combinations of computer components with other non-computer components, reduced capacity computers). It is also to be understood that the examples provided herein may be implemented in various environments (e.g., networked architectures utilizing clients and servers, public and private computer networks, computer networks of commercial on-line services, internal corporate local area networks (LANs), or intranets).

It is to be further appreciated that data storage implementations described herein may be comprised of any types of structures having any arrangements or configurations facilitating desired retrieval, storage and/or searching not departing from the spirit and scope of the present invention (e.g., combination or individual implementation of two dimensional arrays, three dimensional arrays, relational databases, object-oriented databases, object-relational databases, data tables, other searchable structures).

As used in this application, the term component is intended to refer to a computer-related entity (e.g. hardware, a combination of hardware and software, software, software in execution, a process running on a processor, a processor, an object, an executable, a thread of execution, a program, a computer, an application running on a server, a server). Additionally, as used in this application, system is a structure comprising one or more modules. A module is a structure comprising computer hardware and/or software (e.g. computer readable memory encoded with software instructions, computer configuration to carry out specified tasks, application program stored in computer readable memory, server on which an application runs, software object). Due to the nature of modules, multiple modules can be intermingled and are often not separated from one another. Systems can likewise be intermingled and inseparable.

It is to be appreciated that various aspects of the disclosure, e.g. image registration, herein may employ technologies associated with facilitating unconstrained optimization (e.g. back-propagation, Bayesian, Fuzzy Set, Non Linear regression, or other neural network paradigms including mixture of experts, cerebellar model arithmetic computer (CMACS), Radial Basis Functions, directed search networks, and functional link nets).

What has been described above includes exemplary aspects and/or implementations. It is, of course, not possible to describe every conceivable combination of components or methodologies, but one of ordinary skill in the art will recognize that many further combinations and permutations are possible. Accordingly, the disclosure herein is intended to embrace all such alterations, modifications and variations that fall within the spirit and scope of the appended claims.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent. In addition, while a particular feature of the disclosure may have been disclosed with respect to only one of several implementations, such feature may be combined with one or more other features of other implementations as may be desired and advantageous for any given or particular application. Furthermore, to the extent that the terms “includes”, “having”, “has”, “with”, or variants thereof are used in either the detailed description or the claims, such terms are intended to be inclusive in a manner similar to the term “comprising.” Also, “exemplary” as utilized herein merely means an example, rather than the best.

What is claimed is:

1. A method for facilitating stress analysis of a heart, comprising:

receiving volumetric data representing the left ventricle;

registering the volumetric data to obtain at least one of temporally and spatially aligned volumetric data representing the left ventricle;

applying a mesh template to the registered volumetric data to produce at least one mesh comprising a plurality of vertices;

segmenting the registered volumetric data to produce a plurality of left ventricle segments;

associating the vertices of the mesh with the left ventricle segments; and computing a functional quantitative metric based on the at least one mesh and left ventricle segments.

2. The method of claim 1, wherein functional quantitative metric comprises at least one of fractional area change, left ventricle volume, and ejection fraction.

3. The method of claim 1, wherein the volumetric data comprises at least one of CT, MRI, ultrasound, X-ray, PET, and SPECT representations of the left ventricle.

4. The method of claim 1, wherein the registered volumetric data is segmented into between 16 and 17 segments.

5. A computer-readable medium comprising processor-executable instructions configured to perform the method of claim 1.

6. A method for displaying a view of a portion of a heart, comprising:

receiving volumetric data of the left ventricle;

registering the volumetric data to obtain at least one of temporally and spatially aligned volumetric data representing the left ventricle;

applying a mesh template to the registered volumetric data to produce at least one mesh comprising a plurality of vertices; and displaying the view of the portion of the heart on the at least one mesh.

7. The method of claim 6, wherein the volumetric data comprises at least one of CT, MRI, ultrasound, X-ray, PET, and SPECT representations of the left ventricle.

8. The method of claim 6, comprising:

segmenting the registered volumetric data to produce a plurality of left ventricle segments; and associating the vertices of the mesh with the left ventricle segments, wherein the displaying is based on the left ventricle segments.

9. The method of claim 8, wherein the registered volumetric data is segmented into between 16 and 17 segments.

10. The method of claim 8, where in at least one of the segments has an associated identifier.

11. The method of claim 8, wherein the associated identifier comprises a color coding.

12. A computer-readable medium comprising processor-executable instructions configured to perform the method of claim 6.

13. A graphical user interface configured to facilitate stress analysis of a heart utilizing volumetric data representing a plurality of left ventricle segments, the graphical user interface comprising:

a first interface component configured to receive input selecting at least one of the left ventricle segments;

a second interface component configured to receive input representing an assessment related score regarding the at least one selected left ventricle segment; and a third interface component configured to display functional quantitative metrics of the at least one selected left ventricle segment computed with respect to the assessment related score.

14. The graphical user interface of claim 13, wherein the volumetric data comprises at least one of CT, MRI, ultrasound, X-ray, PET, and SPECT representations of the left ventricle.

15. The graphical user interface of claim 13, comprising:

a fourth interface component configured to display a range of at least one functional quantitative metric of the at least one selected left ventricle segment.

16. The graphical user interface of claim 13, comprising:

a fifth interface component configured to display at least one assessment related score computed with regard to at least one selected left ventricle segment.

17. The graphical user interface of claim 13, the third interface component comprising an identifier indicative of the status of the functional quantitative metric of the at least one selected left ventricle segment.

18. The graphical user interface of claim 17, the identifier comprising a color coding.

19. The graphical user interface of claim 17, the status comprising a comparison of the functional quantitative metric with a target range for the functional quantitative metric.

20. A computer-readable medium comprising processor-executable instructions configured to implement the graphical user interface of claim 13.

* * * * *